US006517815B1

United States Patent
Leinen et al.

(10) Patent No.: US 6,517,815 B1
(45) Date of Patent: Feb. 11, 2003

(54) CLEANING AGENT FOR DENTAL USE COMPRISING A COMBINATION OF POLISHING AGENTS BASED ON A SILICIC ACID AND ALUMINUM OXIDE

(75) Inventors: Hans-Theo Leinen, Duesseldorf (DE); Peter Wuelknitz, Leichlingen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/508,660

(22) PCT Filed: Sep. 5, 1998

(86) PCT No.: PCT/EP98/05632

§ 371 (c)(1),
(2), (4) Date: Mar. 16, 2001

(87) PCT Pub. No.: WO99/13851

PCT Pub. Date: Mar. 25, 1999

(30) Foreign Application Priority Data

Sep. 15, 1997 (DE) .......................... 197 40 453

(51) Int. Cl.⁷ .............................. A61K 7/16; A61K 7/18
(52) U.S. Cl. .............................. 424/49; 424/52; 424/57
(58) Field of Search .................... 424/49.58, 49.88

(56) References Cited

U.S. PATENT DOCUMENTS

| 3,003,919 A | * 10/1961 | Broge | 167/93 |
|---|---|---|---|
| 3,060,098 A | * 10/1962 | Gershon | 167/93 |
| 3,538,230 A | 11/1970 | Pader et al. | 424/50 |
| 3,670,076 A | * 6/1972 | Muhler | 424/157 |
| 3,772,269 A | 11/1973 | Lew | 260/210 |
| 3,839,318 A | 10/1974 | Mansfield | 260/210 |
| 3,981,988 A | * 9/1976 | Newman et al. | 424/49 |
| 4,144,322 A | 3/1979 | Cordon et al. | 424/49 |
| 4,153,680 A | 5/1979 | Seybert | 424/49 |
| 4,515,772 A | * 5/1985 | Parran et al. | 424/57 |
| 4,632,826 A | * 12/1986 | Ploger et al. | 424/52 |
| 4,726,943 A | * 2/1988 | Kluepper et al. | 424/54 |
| 4,820,507 A | * 4/1989 | Kluepper et al. | 424/54 |
| 4,822,599 A | * 4/1989 | Mitra | 424/52 |
| 4,857,289 A | 8/1989 | Nauroth et al. | 423/339 |
| 4,913,895 A | * 4/1990 | Miyake et al. | 424/57 |
| 5,094,844 A | 3/1992 | Gaffer et al. | 424/52 |
| 5,145,667 A | * 9/1992 | Ibrahim et al. | 424/52 |
| 5,324,505 A | * 6/1994 | Kornettka et al. | 424/49 |
| 5,480,979 A | 1/1996 | Weuthen et al. | 536/18.6 |
| 5,605,677 A | * 2/1997 | Schumann et al. | 424/52 |
| 5,686,064 A | 11/1997 | Gaffar et al. | |
| 5,698,182 A | 12/1997 | Prencipe et al. | |

FOREIGN PATENT DOCUMENTS

| CA | 1 049 228 | 2/1979 |
|---|---|---|
| CA | 1 259 927 | 9/1989 |
| DE | 20 36 472 | 2/1971 |
| DE | 25 22 486 | 11/1975 |
| DE | 27 58 548 | 7/1978 |
| DE | 31 14 493 | 10/1982 |
| DE | 34 25 152 | 1/1986 |
| EP | 0 077 167 | 4/1983 |
| GB | 2 230 189 | 10/1990 |
| WO | WO93/10132 | 5/1993 |

OTHER PUBLICATIONS

Ullman Encyclopedia der Technischen Chemie, 4th Edition, vol. 7, pp. 298.
Derwent Patent Abstract (WPAT) No. 1986–021939 [04].
Derwent Patent Abstract (WPAT) No. 1978–50101A [28].
Derwent Patent Abstract (WPAT) No. 1975–80588W [49].
Derwent Patent Abstract (WPAT) No. 1982–90652E [43].
Derwent Patent Abstract (WPAT) No. 1971–105828 [06].
Derwent Patent Abstract (WPAT) No. 1993–168483 [21].

* cited by examiner

Primary Examiner—Shep K. Rose
(74) Attorney, Agent, or Firm—Stephen D. Harper; Glenn E. J. Murphy

(57) ABSTRACT

A dentifrice in the form of an aqueous paste or liquid dispersion, comprising 10% to 30% by weight of a combination of silica polishing agents and aluminum oxide in a ratio by weight of 10:0.2 to 10:2, 20% to 50% by weight of a humectant selected from the group consisting of sorbitol, glycerol, 1,2-propylene glycol, and mixtures thereof, and 2% to 12% by weight of a condensed phosphate selected from the group consisting of tripolyphosphate, pyrophosphate, trimetaphosphate, and mixtures thereof. The condensed phosphates are in the form of an alkali metal or ammonium salt.

13 Claims, No Drawings

CLEANING AGENT FOR DENTAL USE COMPRISING A COMBINATION OF POLISHING AGENTS BASED ON A SILICIC ACID AND ALUMINUM OXIDE

CROSS REFERENCE TO RELATED APPLICATIONS

This application is a national stage application under 35 U.S.C. §371 of international application PCT/EP98/05632 filed on Sep. 5, 1998, the international application not being published in English.

BACKGROUND OF THE INVENTION

This invention relates to a dentifrice in the form of a water-containing, paste-form or liquid cream containing 10 to 30% by weight of a combination of polishing agents and 20 to 50% by weight of a humectant, of which the cleaning performance has been further improved by an addition of condensed phosphates Toothpastes are used in the daily cleaning of teeth by brushing with a toothbrush. Toothpastes are intended above all to support the removal from the tooth surfaces of food remains, discoloration, for example by tobacco or tea, and firmly adhering bacterial films, so-called plaque. This is mainly done by the polishing agents present in the toothpaste and, to a lesser extent, also by the surfactants present. In order to develop their cleaning and polishing effect, the polishing agents have to have a certain abrasiveness towards the tooth surface. However, it is extremely important that the abrasiveness towards dental enamel and dentin is kept at low levels to avoid damage to the tooth surface by the daily use of the toothpastes. Above all, the polishing agents used should not cause any deep scratches on the tooth surface. On the contrary, they should have a smoothing effect on any roughness present in the tooth surface.

Condensed phosphates are known from numerous publications as scale inhibitors and as demineralization inhibitors in dentifrices.

The cleaning effect of water-soluble pyrophosphate salts on teeth discolored by tea and coffee is also known from U.S. Pat. No. 4,822,599 A.

Dentifrices containing an abrasive mixture of a silica polishing agent and a calcined aluminium oxide are known as particularly effective tooth cleaning preparations from DE 27 58 548 C2. This document recommends the addition of certain inorganic electrolyte salts to prevent abrasion of the dental enamel. In spite of this, extremely high dentin abrasion values (RDA) and enamel abrasion values (REA) of 300 to 500 were obtained.

Although the abrasion values can be reduced by reducing or omitting the aluminium oxide polishing agent, cleaning performance is significantly impaired at the same time. Accordingly, there was a need to develop a dentifrice which would combine very low abrasiveness (RDA and REA values below 100) with a very good cleaning effect (CRS values of around 100).

DE 34 25 152 describes a combination of polishing agents consisting of a silica polishing agent and a lightly calcined aluminium oxide with which reduced abrasiveness can be combined with a good cleaning effect.

It has now been found that condensed phosphates are ideally suitable for increasing the cleaning performance of toothpastes containing a combination of silica polishing agents and aluminium oxide polishing agents to such an extent that the need stated above is satisfied without any significant increase in the abrasion values.

Accordingly, the present invention relates to dentifrices in the form of water-containing, paste-form or liquid dispersions containing 10 to 30% by weight of a combination of silica polishing agents and aluminium oxide in a ratio by weight of 10:(0.2-2) and 20 to 50% by weight of a humectant from the group consisting of sorbitol, glycerol, 1,2-propylene glycol or mixtures thereof, characterized in that they contain a condensed phosphate from the group consisting of tripolyphosphate, pyrophosphate, trimetaphosphate or mixtures thereof in the form of the alkali metal or ammonium salts in a quantity of 2 to 12% by weight in order to increase the cleaning effect.

Suitable silica polishing agents are, for example, silica gels which are obtained by reacting sodium silicate solutions with strong aqueous mineral acids to form a hydrosol, ageing the hydrosol to form the hydrogel, washing and drying. If drying is carried out under moderate conditions to water contents of 15 to 35% by weight, so-called hydrogel silicas, which are known for example from U.S. Pat. No. 4,153,680, are obtained.

Drying to water contents below 15% by weight results in irreversible shrinkage of the previously loose structure of the hydrogel to the dense structure of the so-called xerogel. Xerogel silicas are described, for example, in U.S. 3,538,230.

A second preferred group of silica polishing agents are the precipitated silicas. Precipitated silicas are obtained by precipitation of silica from dilute alkali metal silicate solutions by addition of strong acids under conditions where aggregation to the sol and gel cannot occur. Suitable processes for the production of precipitated silicas are described, for example, in DE-OS 25 22 486 and in DE-OS 31 14 493. Preferred precipitated silicas are, for example, those which have a mean particle size of 5 to 20 $\mu$m, a sieve residue (45 $\mu$m) of less than 1% by weight and a specific surface (BET) of 100 to 300 $m^2$/g.

By virtue of the special combination of polishing agents, the dentifrices according to the invention have an excellent cleaning effect, even against discoloration of the teeth by tea and nicotine. At the same time, a good polishing effect (smoothing of roughness) is obtained despite only moderate dentin and enamel abrasion. In spite of the presence of a relatively hard polishing component, namely aluminium oxide, the dentifrices according to the invention have hardly any scratching effect.

A preferred aluminium oxide polish is a lightly calcined alumina with a content of at least 10% by weight of $\alpha$-aluminium oxide of various so-called $\gamma$-aluminium oxide modifications.

Suitable lightly calcined aluminas are prepared by calcination from aluminium hydroxide. Aluminium hydroxide is converted by calcination into $\alpha$-$Al_2O_3$ which is thermodynamically stable at temperatures above 1200° C. The thermodynamically unstable $Al_2O_3$ modifications occurring at temperatures of 400 to 1000° C are known as $\gamma$-forms (cf. Ullmann, Enzyclopädie der technischen Chemie, 4th Edition (1974), Vol. 7, page 298). The degree of calcination, i.e. the conversion into the thermodynamically stable $\alpha$-$Al_2O_3$, can be adjusted as required through the choice of the temperature and the duration of the calcination process. Light calcination gives an alumina with a $\gamma$-$Al_2O_3$ content which is lower, the higher the calcination temperature and the longer the calcination time. Lightly calcined aluminas differ from pure $\alpha$-$Al_2O_3$ in the lower hardness of the agglomerates, in a larger specific surface and larger pore volumes.

The dentin abrasion (RDA) of the relatively lightly calcined aluminas to be used in accordance with the invention containing 10 to 50% by weight of γ-$Al_2O_3$ is only 30 to 60% of the dentin abrasion of a heavily calcined, pure α-$Al_2O_3$ (as measured in a standard toothpaste containing 20% by weight alumina as sole polishing agent).

In contrast to α-$Al_2O_3$, γ-$Al_2O_3$ can be dyed red with an aqueous-ammoniacal solution of Alizarin S (1,2-dihydroxy-9,10-anthraquinone-4-sulfonic acid). The degree of dyeability can be used as a measure of the degree of calcination or rather the percentage content of δ-$Al_2O_3$ in a calcined alumina:

Ca. 1 g $Al_2O_3$, 10 ml of a solution of 2 g/l Alizarin S in water and 3 drops of an aqueous 10% by weight solution of $NH_3$ are introduced into a test tube and briefly boiled. The $Al_2O_3$ is then filtered off, washed, dried and examined under a microscope or evaluated by colorimetry.

Suitable lightly calcined aluminas containing 10 to 50% by weight γ-$Al_2O_3$ can be colored pale to deep pink by this method.

Aluminium oxide polishing agents with various degrees of calcination, fineness and bulk densities are commercially obtainable, for example the "Poliertonerden (polishing aluminas)" of Giulini-Chemie and ALCOA.

A particularly suitable quality "Poliertonerde P10 feinst" has an agglomerate size below 20 μm, a mean primary crystal size of 0.5 to 1.5 μm and a bulk density of 500 to 600 g/l.

Sorbitol, xylitol, glycerol, propylene glycol or mixtures of these polyols may be present as humectants. Polyethylene glycols with molecular weights of 400 to 2000 may also be partly present as humectant components. Sorbitol in a quantity of 20 to 40% by weight is preferably present as the humectant.

The condensed phosphates are present in the form of their alkali metal salts, preferably their sodium or potassium salts. The aqueous solutions of these phosphates show an alkaline reaction on account of hydrolytic effects. The dentifrices according to the invention are adjusted to a pH of 7.5 to 9 by addition of an acid. Suitable acids are, for example, citric acid, phosphoric acid or acidic salts, for example $NaH_2PO_4$. However, acidic salts of the condensed phosphates, i.e. for example $K_2H_2P_2O_7$, may also be partly used to adjust the dentifrice to the required pH value.

Mixtures of various condensed phosphates or hydrated salts of the condensed phosphates may also be used. However, the specified quantities of 2 to 12% by weight are based on the water-free salts. A sodium or potassium tripolyphosphate in a quantity of 5 to 10% by weight of the composition is preferably present as the condensed phosphate.

The cleaning effect of the dentifrices according to the invention may be further improved by addition of a suitable surfactant. The addition of a surfactant may also be desirable for producing a foam during brushing of the teeth, for stabilizing the dispersion of polishing agents and for emulsifying or solubilizing the flavoring oils. Suitable surfactants which develop a certain foaming effect are the nonionic surfactants, for example sodium alkyl sulfates containing 12 to 18 carbon atoms in the alkyl group. These surfactants also have a certain enzyme-inhibiting effect on the bacterial metabolism of plaque. Other suitable surfactants are alkali metal salts, preferably sodium salts, of alkyl polyglycol ether sulfate containing 12 to 16 carbon atoms in the linear alkyl group and 2 to 6 glycol ether groups in the molecule, of linear alkane ($C_{12-18}$) sulfonate, of sulfosuccinic acid monoalkyl ($C_{12-18}$) esters, of sulfated fatty acid monoglycerides, sulfated fatty acid alkanolamides, sulfoacetic acid alkyl ($C_{12-16}$) esters, acyl sarcosines, acyl taurides and acyl isethionates containing 8 to 18 carbon atoms in the acyl group.

Zwitterionic and ampholytic surfactants may also be used, preferably in combination with anionic surfactants. However, it is particularly preferred to use nonionic surfactants to promote the cleaning effect. Suitable nonionic surfactants are, for example, products of the addition of ethylene oxide with fatty alcohols, with fatty acids, with fatty acid monoglycerides, with sorbitan fatty acid monoesters or with methyl glucoside fatty acid monoesters. The quantity of ethylene oxide added on should be so large that the surfactants are soluble in water, i.e. at least 1 g/l should be soluble in water at 20° C. Another group of suitable surfactants are the alkyl (oligo)glycosides containing 8 to 16 carbon atoms in the alkyl group and having a degree of oligomerization of the glycoside unit of 1 to 4. Alkyl (oligo)glycosides, their production and use as surfactants are known, for example, from U.S. Pat. No. 3,839,318, DE-A-20 36 472, EP-A-77 167 or WO-A-93/10132.

So far as the glycoside unit is concerned, monoglycosides (x=1) where a monosaccharide unit is attached to a $C_{10-16}$ fatty alcohol by a glycoside linkage and oligomeric glycosides with a degree of oligomerization x of up to 10 are suitable. The degree of oligomerization is a statistical mean value on which the homolog distribution typical of such technical products is based.

A particularly suitable alkyl (oligo)glycoside is an alkyl (oligo)glucoside with the formula $RO(C_6H_{10}O)_x$—H, where R is an alkyl group containing 12 to 14 carbon atoms and x has a mean value of 1 to 4.

A nonionic solubilizer from the group of surface-active compounds may be necessary, particularly for solubilizing the generally water-insoluble flavoring oils. Particularly suitable nonionic solubilizers are, for example, ethoxylated fatty acid glycerides, ethoxylated fatty acid sorbitan partial esters or fatty acid partial esters of glycerol or sorbitan ethoxylates. Solubilizers from the group of ethoxylated fatty acid glycerides include above all products of the addition of 20 to 60 moles of ethylene oxide onto monoand diglycerides of linear fatty acids containing 12 to 18 carbon atoms or onto glycerides of hydroxy fatty acids, such as hydroxystearic acid or ricinoleic acid. Other suitable solubilizers are ethoxylated fatty acid sorbitan partial esters, i.e. preferably products of the addition of 20 to 60 moles ethylene oxide onto sorbitan monoesters and sorbitan diesters of fatty acids containing 12 to 18 carbon atoms. Other suitable solubilizers are fatty acid partial esters of glycerol or sorbitan ethoxylates, i.e. preferably monoesters and diesters of $C_{12-18}$ fatty acids and products of the addition of 20 to 60 moles ethylene oxide onto 1 mole glycerol or onto 1 mole sorbitol.

The dentifrices according to the invention preferably contain products of the addition of 20 to 60 moles ethylene oxide onto hydrogenated or non-hydrogenated castor oil (i.e. onto hydroxystearic acid or ricinoleic acid triglyceride), onto glycerol monostearate and/or distearate or onto sorbitan monostearate and/or distearate as solubilizers for any flavoring oils present.

Suitable flavoring components are, for example, sweeteners and/or flavoring oils. Suitable flavoring oils are any of the natural and synthetic flavors typically used in oral and dental care preparations. Natural flavors may be used both in the form of the essential oils isolated from the drugs and in the form of the individual components isolated therefrom. The dentifrice should preferably contain at least one flavoring oil from the group consisting of peppermint oil, spearmint oil, anise oil, Japanese anise oil, caraway oil, eucalyptus oil, fennel oil, cinnamon oil, clove oil, geranium oil, sage oil, pimento oil, thyme oil, marjoram oil, basil oil, citrus oil, gaultheria oil or one or more components of these oils isolated from them or synthetically produced. The most important components of the oils mentioned are, for example, menthol, carvone, anethol, cineol, eugenol, cinnamaldehyde, caryophyllene, geraniol, citronellol, linalool, salvia, thymol, terpinene, terpineol, methyl chavicol and methyl salicylate. Other suitable flavors are, for example, menthyl acetate, vanillin, ionone, linalyl acetate, rhodinol and piperitone.

In addition, the dentifrices according to the invention may contain a therapeutic agent for controlling caries, scale, parodontitis or other diseases of the mouth and teeth. An active principle preferably present is a caries-inhibiting fluorine compound, preferably from the group of fluorides or monofluorophosphates in a quantity of 0.1 to 0.5% by weight fluorine. Suitable fluorine compounds are, for example, sodium fluoride, potassium fluoride, tin fluoride, sodium monofluorophosphate ($Na_2PO_3F$), potassium monofluorophosphate or the fluoride or an organic amino compound.

Other suitable therapeutic agents are, for example scale inhibitors, for example organophosphates, such as 1-azacycloheptane-2,2-diphosphonic acid (Na salt) or 1-hydroxyethane-1,1-diphosphonic acid (Na salt), and anti-microbial plaque inhibitors such as, for example, hexachlorophene, chlorhexidine, hexetidine, triclosan, bromochlorophene, phenyl salicylate. Substances effective in promoting remineralization and the closure of dental lesions, for example dicalcium phosphate dihydrate, preferably in combination with magnesium ions, may also be present in the dentifrices according to the invention.

In one preferred embodiment, the toothpastes according to the invention additionally contain, for example, 1 to 10% by weight of dicalcium phosphate dihydrate (brushite) and 0.1 to 0.5% by weight of magnesium ions, preferably in the form of a water-soluble magnesium salt, for example magnesium sulfate, magnesium fluoride or magnesium monofluoro-phosphate.

Finally, the toothpastes according to the invention may contain other components which are normally encountered in dentifrices and which do not reduce the effects according to the invention. Such typical toothpaste additives are, for example, other polishing agents in relatively small quantities of, for example, 1 to 10% by weight, for example calcium carbonate (chalk), insoluble sodium metaphosphate, calcium pyrophosphate, hydroxyl apatite, aluminium hydroxide, sodium aluminium silicates (zeolite A) or particulate organic polymers, for example polymethacrylate, pigments, for example titanium dioxide or zinc oxide, dyes, pH regulators and buffers, for example sodium citrate or sodium bicarbonate, sodium benzoate, wound-healing and anti-inflammatory agents such as, for example, allantoin, urea, panthenol, azulene or camomile extract, preservatives such as, for example, sorbic acid salts, p-hydroxybenzoic acid ester.

The following Examples are intended to illustrate the invention.

EXAMPLES

The following toothpastes were prepared:

| Composition | 1 | 2 | 3 | 4 | 5 |
|---|---|---|---|---|---|
| Sident 8 (1) | 14.0 | — | — | — | — |
| Sorbosil AC 39 (2) | — | 14.0 | — | — | 14.0 |
| Zeodent 113 (3) | — | — | 14.0 | — | — |
| Zeodent 623 (4) | — | — | — | 14.0 | — |
| Poliertonerde P10 feinst (5) | 1.0 | 1.0 | 1.0 | 1.0 | 0.5 |
| $Na_5P_3O_{10}$ (Na tripolyphosphate) | 5.0 | 5.0 | 5.0 | 5.0 | 5.0 |
| $Na_2PO_3F$ (Na monofluorophosphate) | — | 0.8 | — | — | — |
| NaF | 0.24 | — | 0.24 | 0.24 | 0.24 |
| Na saccharinate | 0.1 | 0.1 | 0.1 | 0.1 | 0.1 |
| Titanium dioxide | 0.5 | 0.5 | 0.5 | 0.5 | 0.5 |
| PHB methyl ester | 0.1 | 0.1 | 0.1 | 0.1 | 0.1 |
| Carboxymethyl cellulose | 1.25 | 1.25 | 1.25 | 1.25 | 1.25 |
| Sorbitol (70%) | 32.0 | 32.0 | 32.0 | 32.0 | 32.0 |
| 1,2-Propylene glycol | 5.0 | 5.0 | 5.0 | 5.0 | 5.0 |
| Cremophor RH 60 (7) | 1.0 | — | 1.0 | 1.0 | 1.0 |
| Arlatone289 (8) | — | 1.0 | — | — | — |
| Flavoring oil | 0.8 | 0.8 | 0.8 | 0.8 | 0.8 |
| Water | to 100 | to 100 | to 100 | to 100 | to 100 |

| Composition | 6 | C1 | C2 | C3 |
|---|---|---|---|---|
| Sorbisil AC 39 (2) | 14 | 14 | 14 | 14 |
| Poliertonerde P 10 feinst (5) | 1 | — | — | — |
| Precarb 100 (6) | — | 2 | 2 | 2 |
| $Na_5P_3O_{10}$ | 10 | 10 | 5 | 0 |
| $Na_2PO_3F$ | 0.8 | 0.8 | 0.8 | 0.8 |
| NaF | — | — | — | — |
| Na saccharinate | 0.1 | 0.1 | 0.1 | 0.1 |
| Titanium dioxide | 0.5 | 0.5 | 0.5 | 0.5 |
| PHB methyl ester | 0.1 | 0.1 | 0.1 | 0.1 |
| Carboxymethyl cellulose | 1.25 | 1.25 | 1.25 | 1.25 |
| Sorbitol (70%) | 32.0 | 32.0 | 32.0 | 32.0 |
| 1,2-Propylene glycol | 5.0 | 5.0 | 5.0 | 5.0 |
| Arlatone 289 (8) | 1.0 | 1.0 | 1.0 | 1.0 |
| Flavoring oil | 0.8 | 0.8 | 0.8 | 0.8 |
| Water | to 100 | to 100 | to 100 | to 100 |

The following commercial products were used:

(1) Sident ® 8 (DEGUSSA) — silica polish
mean particle size: 10.0 μm
sieve residue (45 μm): ≦0.3%
compacted bulk density: 300 g/l (2) Sorbosil AC 39 (Crosfield Ltd.) — silica polish
particle size: 9–13 μm (3) Zeodent 113 (Huber Chemicals) — silica polish
mean particle size: 12 μm
sieve residue (45 μm): 1.0% max.
spec. surface (BET): 150 m²/g (4) Zeodent 623 (Huber Chemicals) — silica polish
mean particle size: 12 μm
sieve residue (45 μm): 0.5% max.
spec. surface (BET): 250 m²/g (5) Poliertonerde P10 feinst (Giulini Chemie) — aluminium oxide polish
mean agglomerate size: <20 μm (min. 99%)
primary particle size: ca. 1 μm
degree of calcination: low (6) Precarb 100 — calcium carbonate (chalk)
compacted bulk density 0.5 g/ml
spec. surface: 9.0 m²/g (7) Cremophor RH 60 — hydr. castor oil + 60 moles EO (8) Arlatone 289 — hydr. castor oil + 54 moles EO
melting point: 39° C.
HLB value: 14.4

Determination of the cleaning effect (CRS)

Method

The surface of bovine teeth was conditioned, stained with tea under defined conditions and cleaned with the toothpaste to be tested under defined conditions. The lightening in color obtained was measured by colorimetry and was compared with the lightening effect of a standard toothpaste.

Sample Preparation

Bovine incisors were cut into 7×7 mm blocks which were then mounted with wax on Plexiglas squares (1×2.5×2.5 cm) in such a way that only the enamel surface was exposed. The enamel surface was polished until it appeared uniformly smooth.

Sample Conditioning

The mounted tooth blocks were successively immersed in 0.12 N hydrochloric acid (60 seconds), saturated $Na_2CO_3$ solution (120 seconds) and in 1% phytic acid solution (60 seconds). After each treatment, the samples were rinsed with deionized water and dried by blotting with absorbent paper. The tooth samples were then fixed to the staining apparatus and moved for 5 days through a solution of black tea at 20° C. The tea solution had been prepared by extracting a 1.5 g teabag with 300 g of boiling water (10 minutes) and was renewed twice a day.

Polishing Tests

The mounted tooth blocks were then placed in a Grabenstetter V8 brushing machine and were brushed in a toothpaste suspension of 20 g paste and 40 g deionized water using a soft Oral-B toothbrush (pressure applied 150 g). A suspension of 10 g of calcium pyrophosphate in 50 g of swollen carboxymethyl cellulose (0.5% CMC, 10% glycerol, 89.5% water) was used as the polishing standard. The cleaning effect of this standard is defined as the 100% value.

Measurement of the Cleaning Effect

The lightening effect was measured to DIN 5033 using a Dr. Lange color difference measuring instrument (type Micro Color (DC 8334)). A xenon lamp producing D 65 standard light corresponding to daylight was used. Barium sulfate was used as the color standard.

Double measurements of a circular area 7 mm in diameter on the sample surface were carried out. Eight stained tooth samples were used for each toothpaste and average values were formed. The test parameter used was the standard color value Y determined to DIN 5033 which is a measure of the lightness of a color.

Lightness measurement was carried out after 1000 brush strokes. The cleaning effect CRS (cleaning ratio soft) is calculated as follows:

$$CRS\ [\%] = \frac{\text{average standard color value } Y - \text{increment test paste}}{\text{average standard color value } Y - \text{increment polishing standard}} \cdot 100\ [\%]$$

Determination of Abrasiveness (RDA)

Abrasiveness was determined by the RDA method (radioactive dentin abrasion) using the Grabenstetter process of Missouri Analytical Laboratories, St. Louis, Mo. (cf. J. Dent. Res. 17, 1060–1068 (1958).

Results

| Example | 1 | 2 | 3 | 4 | 5 | 6 | C1 | C2 | C3 |
|---|---|---|---|---|---|---|---|---|---|
| CRS % | 90 | 88 | 103 | 98 | 73 | 97 | 80 | 64 | 31 |
| RDA % | n.d.* | 66 | 55 | 95 | 69 | n.d. | n.d. | 57 | n.d. |

(*n.d. not determined)

The results show that, without aluminium oxide (C1–C3), a weaker cleaning effect is obtained than with the toothpastes according to the invention (1–4), despite high Na tripolyphosphate contents (C1), and that dentin abrasion shows hardly any increase in relation to the comparison pastes despite the high cleaning performance.

What is claimed is:

1. A dentifrice in the form of anqueous paste or liquid dispersion, comprising
   (a) 10% to 30% by weight of a combination of one or more silica polishing agents and aluminum oxide in a ratio by weight of 10:0.2 to 10:2, said aluminum oxide comprising at least 10% by weight of γ-aluminum oxide, based on the total weight of said aluminum oxide;
   (b) 20% to 50% by weight of a humectant selected from the group consisting of sorbitol, glycerol, 1,2-propylene glycol, polyethylene glycols, and mixtures thereof; and
   (c) 2% to 12% by weight of a condensed phosphate selected from the group consisting of tripolyphosphate, pyrophosphate, trimetaphosphate, and mixtures thereof, said condensed phosphates being in the form of an alkali metal or ammonium salt, wherein the percentages of the combination of the silica polishing agent and aluminum oxide, the humectant and the condensed phosphate are based on the total weight of the composition.

2. The dentifrice of claim 1, wherein the aluminum oxide comprises lightly calcined alumina containing 10% to 50% by weight of γ-aluminum oxide.

3. The dentifrice of claim 1, comprising 25% to 40% by weight of sorbitol.

4. The dentifrice of claim 2, comprising 25% to 40% by weight of sorbitol.

5. The dentifrice of claim 1, comprising 5% to 10% by weight of sodium or potassium tripolyphosphate.

6. The dentifrice of claim 2, comprising 5% to 10% by weight of sodium or potassium tripolyphosphate.

7. The dentifrice of claim 4, comprising 5% to 10% by weight of sodium or potassium tripolyphosphate.

8. The dentifrice of claim 1, wherein the silica polishing agents comprise precipitated silica with a particle size of 5 to 20 μm and a specific surface of 100 to 300 g/l.

9. The dentifrice of claim 7, wherein the silica polishing agents comprise precipitated silica with a particle size of 5 to 20 μm and a specific surface of 100 to 300 g/l.

10. The dentifrice of claim 1, comprising 0.1% to 0.5% by weight of fluorine.

11. The dentifrice of claim 2, comprising 0.1% to 0.5% by weight of fluorine.

12. The dentifrice of claim 4, comprising 0.1% to 0.5% by weight of fluorine.

13. The dentifrice of claim 9, comprising a fluoride or monofluorophosphates such that the dentifrice comprises 0.1% to 0.5% by weight of fluorine.

* * * * *

UNITED STATES PATENT AND TRADEMARK OFFICE
CERTIFICATE OF CORRECTION

PATENT NO. : 6,517,815 B1
DATED : February 11, 2003
INVENTOR(S) : Leinen et al.

It is certified that error appears in the above-identified patent and that said Letters Patent is hereby corrected as shown below:

Column 8,
Line 17, delete "anqueous", and insert therefore -- an aqueous --.

Signed and Sealed this

Fifth Day of October, 2004

JON W. DUDAS
*Director of the United States Patent and Trademark Office*